United States Patent [19]

Wajaroff

[11] 4,331,167

[45] May 25, 1982

[54] COMPOSITIONS AND METHODS FOR PERMANENT WAVING OF HAIR

[75] Inventor: Theodor Wajaroff, Darmstadt, Fed. Rep. of Germany

[73] Assignee: Wella Aktiengesellschaft, Darmstadt, Fed. Rep. of Germany

[21] Appl. No.: 120,075

[22] Filed: Feb. 7, 1980

[30] Foreign Application Priority Data

Feb. 12, 1979 [DE] Fed. Rep. of Germany ....... 2905257

[51] Int. Cl.³ ........................... A45D 7/00; A61K 7/09
[52] U.S. Cl. .......................................... 132/7; 424/70; 424/71; 424/DIG. 1; 424/DIG. 2; 524/106; 524/269
[58] Field of Search ..................... 424/70, 71, DIG. 1, 424/DIG. 2; 260/33.4 R; 132/7

[56] References Cited

U.S. PATENT DOCUMENTS 3,964,500  6/1976  Drakoff ....................... 424/DIG. 2

*Primary Examiner*—Alan L. Rotman
*Attorney, Agent, or Firm*—Michael J. Striker

[57] ABSTRACT

A composition adapted for application to hair before the hair is wound upon curlers and treated for permanent waving thereof comprising:

(a) at least one methylpolysiloxane having a boiling point in the range of 100° to 190° C. and/or at least one paraffin or isoparaffin having a boiling point in the range of 100° to 190° C.,
(b) at least one cation active, non-capillary active compound, and
(c) at least one ampholytic, capillary active imidazoline compound.

17 Claims, No Drawings

COMPOSITIONS AND METHODS FOR PERMANENT WAVING OF HAIR

BACKGROUND OF THE INVENTION

This invention relates to the art of waving hair to produce so-called permanent waves and more particularly relates to a composition adapted for application to the hair before the hair is wound up on the curlers and treated to produce so-called permanent waves.

In the art of permanent waving of the hair with reducing permanent wave solutions, the conventional process as carried out today comprises first washing the hair, subjecting the washed hair to towel drying, dividing the hair up into sections or strands. These strands are then individually wound up on the curlers or rollers under tension and thereafter the hair is moistened or saturated with the reducing or permanent wave solution.

This aforesaid procedure represents a departure from an older process wherein the permanent wave solution is applied onto the hair before it is wound up on the permanent wave rollers and as compared to this older process has numerous advantages. One particularly important advantage is that the newer procedure avoids having the beautician's or hair dresser's hands in contact with the alkaline solution employed for permanent waving for the approximately 20 or more minutes required to wind the hair onto the rollers. Another very important advantage is that it is thereby avoided that the alkaline solution employed for temporarily softening the hair, have the additional time to deleteriously affect the hair, in that in the time required for the winding, the alkaline solution leaches out the natural oils of the hair. Further in the winding up of the hair treated with the permanent wave solution, the hair which is already softened is over stretched giving rise frequently to the breaking of the hair shafts and even to the falling out of the hair. Hair is highly elastic and if the permanent wave solution is applied first, the winding up of the separated hair strands has to be carried out with as little pulling or tension as possible but above all with the tension being applied as far as is possible in a uniform manner. As can be appreciated this is very difficult to effect.

It has already been proposed that so-called end papers be used to lessen the deleterious effects of the winding up of the permanent wave solution moistened hair onto the curlers. In this procedure, the hair ends are placed between a folded thin cellulosic sheet material, for example paper and together with the paper wound up on the roller.

After the permanent wave solution has remained on the hair for the time required for the reducing effect to be achieved and for the desired degree of curl to be imparted to the hair, the time varying according to the nature, condition and quantity of the hair, but amounting to about 10 to 30 minutes, the hair is thoroughly rinsed with water, treated with an oxidizing agent, for example with a peroxide solution, removed from the curlers, again rinsed with water, set in the desired manner and the final drying of the hair is then completed.

Normal hair has different uptake capacities for the permanent wave solution along its length, i.e., the roots have a different uptake capability for the permanent wave solution than do the hair ends. Thus the hair ends are more readily softened by the permanent wave solution with the result that the ends are more strongly waved. The importance of this lies in the fact that it is normal hair growth rather than relaxation which finally destroys the wave. By being able to wave close to the hair roots, several weeks or even months in the case of slow growing hair are added to the useful life of the wave. Unfortunately, this doesn't happen in the case where the permanent wave is carried out by the known procedure, as in order to set the desired wave at the root ends, the opposite ends are over waved. The natural texture and elasticity of the hair are adversely affected with brittleness, breaking and splitting of the hair taking place. This is reinforced in that it cannot be avoided that the hair ends which are directly on the roller are in regard to the total hair strand most strongly stretched, i.e., most tightly wound and therewith most strongly waved.

In accordance with the invention it has now been found that the aforenamed disadvantages can be obviated and a better and more satisfactory permanent waving of the hair carried out, with all of the natural oils and lustre of the hair preserved if there is applied onto the washed hair before it is wound up onto the permanent wave rollers a composition comprising:

(a) at least one methylpolysiloxane having a boiling point in the range of 100° to 190° C. and/or at least one paraffin or isoparaffin having a boiling point in the range of 100° to 190° C., (b) at least one cation active non-capillary active compound, and (c) at least one ampholytic, capillary active imidazoline compound.

In the aforesaid compositions, as methylpolysiloxane, there may be suitably used hexamethyldisiloxane, octamethyltrisiloxane, decamethyltetrasiloxane or the like.

As examples of suitable paraffins and isoparaffins, there may be mentioned in particular, n-nonane, n-decane, methylheptane (isomeric mixture having a boiling point of about 118° C.), trimethylpentane (isomeric mixture having a boiling point of 100°–114° C.) and 2.2.3.3-tetramethylbutane.

As cation active, non-capillary active compounds which can be suitably included in the composition of the invention, there come into consideration (a) cation active resins preferably polymeric dimethylaminoethylmethacrylate (homopolymer, quaternized up to 75% with dimethylsulfate) and polymeric diallyldimethylammoniumchloride;

(b) cation active cellulose having the following formula:

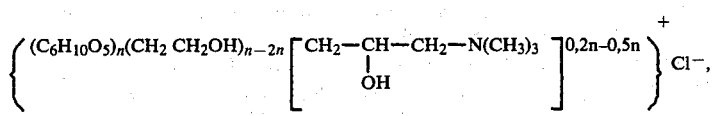

n = 500–2500

As ampholytic, capillary active imidizoline compound there is required to be present at least one imidazoline derivative having the formula

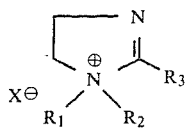

wherein X is OH, Cl, $\frac{1}{2}SO_4$, alkylsulfate, preferably ethyl sulfate and the groups $R_1$, $R_2$ and $R_3$ have the following meanings:

| | | |
|---|---|---|
| $R_1$ = | $-CH_2-COOA$ | A = H, Na |
| | $-CH_2-CH_2-OH$ | |
| $R_2$ = | $-CH_2-CH_2-O-CH_2-COOA$ | A = H, Na |
| | $-CH_2-COOA$ | |
| | $-CH_2-CH_2-OA$ | |
| $R_3$ = | straight chain hydrocarbon groups having 7 to 17 carbon atoms, preferably $C_7H_{15}$, $C_9H_{19}$, $C_{11}H_{23}$, $C_{17}H_{35}$. | |

The methylsiloxane, paraffin and isoparaffin are suitably present in the compositions of the invention in a total concentration of 5 to 60 weight percent, preferably 25 to 55 weight percent. The content of cation active, non-capillary active compound, as well as of the ampholytic capillary active imidazoline compound in the composition amounts to 0.02 to 3.0 weight percent and preferably 0.2 to 3.0 weight percent, with the proviso that the amount of capillary active imidazoline compound does not exceed the amount of the cation active, non-capillary active compound.

The compositions of the invention can additionally contain the usual cosmetic adjuvants, as for instance, alcohols, preferably ethanol, propanol and isopropanol, solvent facilitators, such as oxyethylated castor oil and 4-n-nonylphenoldecaglycol ether, as well as the conventional hair swelling promoters such as urea and alkalisulfites, further alkalinizing agents such as ammonia, monoethanolamine, ammonium hydrogen carbonate and ammonium carbonate, additional capillary active cation active compounds as for example, hexadecyltrimethylammoniumchloride, dyestuffs, perfume oils, glycerin, lanolin and other like hair treatment composition additives. Additionally there can be present in the compositions of the invention an enzyme, as for example urease, lipase or brewer's yeast.

The hair treatment compositions as above disclosed exist as two liquid phases, wherein the upper phase comprises those components mentioned as coming within (a) i.e., methylpolysiloxane, paraffin and/or isoparaffin, while the components mentioned under (b) and (c) i.e., cation active, noncapillary active and ampholytic, capillary active imidazoline derivative are to be found in the lower aqueous phase.

The use of the hair treatment compositions of the invention takes place, by, directly before use, shaking the compounds (a), (b) and (c) in a closed container so that they form together a more or less easily broken emulsion. The resulting emulsion (the hair treatment composition of the invention) is then uniformly applied onto the already washed, towel dried hair. For achieving a satisfactory permanent waving of the hair, there is used depending on the hair body, fullness and abundance about 15 to 25 g of the composition. Thereafter the hair is combed through and divided into strands, which are then rolled upon the rollers and subjected to the customary permanent wave treatment, that is, the hair is then treated with the permanent wave solution. After it has assumed the desired curl or wave, it is released from the rollers and the waving operation is completed.

The advantages of the use of the composition of the invention lie therein that they facilitate the combing of the hair, the dividing of the hair into the sections or strands, as well as the winding up of the hair onto the rollers. Further, the action of the permanent waving composition on the hair ends is reduced and thereby the compositions of the invention permit the uniform waving of the hair from the roots to the ends. The permanent wave comes out with the hair softer, with more natural life, more lustrous, resilient and susceptible of better styling.

In a further understanding of the nature and objects of the invention, reference should be had to the following examples which are given merely to further illustrate the invention and which are not to be construed in a limiting sense.

EXAMPLE 1

Composition, suitable for all hair types

| | |
|---|---|
| 10.0 g | hexamethyldisiloxane |
| 0.3 g | homopolymer of dimethylaminoethyl-methacrylate, quaternized up to 75% with dimethylsulfate |
| 0.1 g | 2-coco-1-sodiumcarboxymethl-1-(2-hydroxyethyl)-imidazoliniumhydroxide |
| 0.3 g | 4-n-nonylphenoldecaglycolether |
| 4.0 g | urea |
| 0.1 g | perfume oil |
| 10.2 g | water |
| 25.0 g | |

EXAMPLE 2

Composition for normal hair

| | |
|---|---|
| 8.0 g | methylheptane, isomeric mixture having a boiling point of about 118° C. |
| 0.1 g | cation active cellulose having the formula $\{(C_6H_{10}O_5)_n(CH_2CH_2OH)_{n-2n}$ $[CH_2CHOHCH_2N(CH_3)_3]_{0,2n-0,5n}\}^+Cl^-$ n = 500 – 2500 |
| 0.1 g | 2-nonyl-1-sodium carboxymethyl-1-[2-(sodium carboxy-methoxy)ethyl]-imidazoliniumhydroxide. |
| 0.1 g | castor oil, oxyethylated with 40 mol ethyleneoxide |
| 0.2 g | perfume oil |
| 6.5 g | water |
| 15.0 g | |

EXAMPLE 3

Composition for normal hair

| | |
|---|---|
| 8.0 g | mixture of isoparaffins having a boiling point of 170–190° C. |
| 0.05 g | copolymerizate of 80% vinylpyrrolidone and 20% dimethylaminoethylmethacrylate (partially quaternized) |
| 0.05 g | 2-heptadecyl-1-carboxymethyl-1-(2-hydroxyethyl-imidazoliniumchloride |
| 0.20 g | hexadecyltrimethylammoniumchloride |
| 0.30 g | perfume oil |
| 9.40 g | water |

EXAMPLE 4

Composition for damaged hair

| | |
|---|---|
| 5.00 g | octamethyltrisiloxane |
| 0.20 g | homopolymer of diallyldimethylammonium chloride |
| 0.15 g | equimolar mixture of 2-heptadecyl-1-carboxymethyl-1-(2-hydroxyethyl)-imidazoliniumchloride and 2-heptadecyl-1-di(2-hydroxyethyl)-imidazoliniumchloride. |
| 3.00 g | isopropanol |
| 0.10 g | perfume oil |
| 11.55 g | water |
| 20.00 g | |

EXAMPLE 5

Composition for bleached hair

| | |
|---|---|
| 5.0 g | octamethyltrisiloxane |
| 5.0 g | decamethyltetrasiloxane |
| 0.6 g | homopolymer of diallyldimethyl ammonium-chloride |
| 0.2 g | 2-undecyl-1-sodium carboxymethyl-1-[2-(sodium-carboxymethoxy) ethyl]-imidazoliniumhydroxide |
| 0.2 g | perfume oil |
| 9.0 g | water |
| 20.0 g | |

All values given in terms of percent are percentages by weight.

I claim:

1. A composition for application to hair before the hair is wound up on curlers and treated for the permanent waving thereof comprising:
   (a) a methylpolysiloxane having a boiling point in the range of 100° to 190° C. selected from the group consisting of hexamethyldisiloxane, octamethyltrisiloxane and decamethyltetrasiloxane, and/or a liquid paraffin and/or liquid isoparaffin having a boiling point in the range of 100°-190° C.,
   (b) a cation active, non-capillary active compound, and
   (c) 0.02 to 3.0 weight % of an ampholytic capillary active imidazoline compound.

2. A composition according to claim 1 wherein said cation active, non-capillary active compound is a cation active cellulose compound having the formula

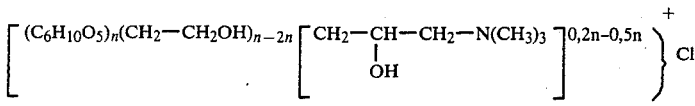

wherein n=500–2500.

3. A composition according to claim 1 wherein said cation active non-capillary active compound is selected from the group counting of polydimethylaminoethyl methacrylate (quaternized up to 75% with dimethylsulfate), a copolymerizate of 80% vinylpyrrolidone/20% dimethylamino ethylmethacrylate (partially quaternized) and polyalkyldimethylammoniumchloride.

4. A composition according to claim 1 additionally containing at least one member selected from the group consisting of ethanol, propanol, isopropanol, oxyethylated castor oil, 4-n-nonyl-phenoldecaglycolether, urea, alkali sulfites, ammonia, monoethanolamine, ammonium hydrogen carbonate, ammonium carbonate hexadecyltrimethylammoniumchloride, dyestuffs, perfume oils, glycerine, lanolin, urease, lipase and brewers yeast.

5. A composition according to claim 1 wherein said paraffin is a member selected from the group consisting of n-nonane and n-decane and said isoparaffin is a member selected from the group consisting of methylheptane (isomeric mixture having a boiling point of about 118° C.), trimethylpentane (isomeric mixture having a boiling point of 100°–114° C.) and 2.2.3.3-tetramethylbutane.

6. A composition according to claim 1 wherein said ampholytic, capillary active imidazoline compound has the following formula

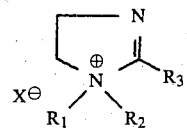

wherein
X is OH, Cl, $\frac{1}{2}SO_4$, or alkylsulfate,
$R_1$ is $-CH_2-COOA$ or $-CH_2-CH_2-OH$, wherein A is H or Na, $R_2$ is $-CH_2-CH_2-O-CH_2-COOA$,
$-CH_2-COOA$ or $-CH_2-CH_2-OA$, wherein A is H or Na and $R_3$ is a straight chain hydrocarbon group having 7-17 carbon atoms.

7. A composition according to claim 6 wherein X is ethylsulfate.

8. A composition according to claim 6 wherein $R_3$ is $C_7H_{15}$, $C_9H_{19}$, $C_{11}H_{23}$ or $C_{17}H_{35}$.

9. A composition according to claim 1 wherein the total amount of component (a) present in said composition amounts to 5 to 60 weight %, said components (b) and (c) each being present in an amount of 0.02–3.0 weight %, with the proviso that the amount of said component (c) does not exceed said component (b).

10. A composition according to claim 9 wherein the total amount of said component (a) in said composition amounts to 25–55 weight percent.

11. A composition according to claim 9 wherein said components (b) and (c) each are present in an amount of 0.2 to 3.0 wt. %.

12. A composition according to claim 1 comprising hexamethyldisiloxane,
homopolymer of dimethylaminoethylmethacrylate (quaternized up to 75% with dimethylsulfate),
2-coco-1-sodiumcarboxymethyl-1-(2-hydroxyethyl)-imidazolinium hydroxide,
4-n-nonyl-phenoldecaglycolether,
urea
perfume oil, and
water 13. A composition according to claim 1 comprising methylheptane (isomeric mixture b.p. about 118° C.), cation active cellulose having the formula

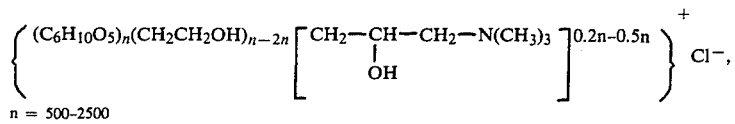

2-nonyl-1-sodiumcarboxymethyl-1[2-(sodiumcarboxymethoxy)-ethyl]-imidazolinium hydroxide, castor oil (oxyethylated with 40 mol ethylene oxide), perfume oil, and water.

14. A composition according to claim 1 comprising mixture of isoparaffins b.p. 170°–190° C. copolymerizate of 80% vinylpyrrolidone and 20% dimethylaminoethylmethacrylate (partially quaternized), 2-heptadecyl-1-carboxymethyl-1-(2-hydroxyethyl)-imidazoliniumchloride, hexadecyltrimethylammoniumchloride, perfume oil and water.

15. A composition according to claim 1 comprising octamethyltrisiloxane, homopolymer of diallyldimethylammonium chloride, equimolar mixture of 2-heptadecyl-1-carboxy-methyl-1-(2-hydroxyethyl)-imidazoliniumchloride and 2-heptadecyl-n-di-(2-hydroxyethyl)-imidazolinium chloride, isopropanol, perfume oil and water.

16. A composition according to claim 1 comprising octamethyltrisiloxane, decamethyltetrasiloxane, homopolymer of diallyldimethyl ammonium-chloride, 2-undecyl-1-sodium carboxymethyl-1-[2-(sodium carboxymethoxy) ethyl]-imidazoliniumhydroxide, perfume oil and water.

17. A method for the permanent waving of hair comprising directly before use forming the composition of claim 1 by shaking together the components a, b and c in a closed container so that there is formed a more or less easily broken emulsion, applying about 15 to 25 g of the resulting emulsion onto washed and towel dried hair, combing the hair with said emulsion applied thereof, dividing the hair into strands, rolling the strands onto rollers, treating the hair with a permanet waving solution and after it has assumed the desired wave, removing the rollers.

* * * * *